(12) United States Patent
Tang et al.

(10) Patent No.: US 8,476,492 B2
(45) Date of Patent: *Jul. 2, 2013

(54) **METHOD OF UTILIZING THE PTS GENE AND ANTI-SENSE ADS TO INCREASE PATCHOULI ALCOHOL CONTENT IN *ARTEMISIA ANNUA* L**

(75) Inventors: Ke Xuan Tang, Shanghai (CN); Yue Yue Wang, Shanghai (CN); Yue Li Tang, Shanghai (CN); Dong-Fang Chen, Shanghai (CN)

(73) Assignee: Firmenich Aromatics (China) Co., Ltd., Shanghai (CN)

( * ) Notice: Subject to any disclaimer, the term of this patent is extended or adjusted under 35 U.S.C. 154(b) by 271 days.

This patent is subject to a terminal disclaimer.

(21) Appl. No.: 13/152,725

(22) Filed: Jun. 3, 2011

(65) Prior Publication Data

US 2011/0300547 A1 Dec. 8, 2011

Related U.S. Application Data

(60) Provisional application No. 61/354,585, filed on Jun. 14, 2010, provisional application No. 61/352,549, filed on Jun. 8, 2010.

(51) Int. Cl.
*C12N 15/82* (2006.01)
*C12Q 1/68* (2006.01)
*G01N 30/02* (2006.01)

(52) U.S. Cl.
USPC .......... 800/285; 800/278; 800/294; 435/6.12; 73/61.52

(58) Field of Classification Search
None
See application file for complete search history.

(56) References Cited

PUBLICATIONS

Wu et al, 2006, Nat. Biotech., 24:1441-1447.*
Huang et al., "T-DNA Insertional Mutation of *Trichoderma harzianum* Mediated by Agrobacterium tumefaciens and Characteristic Analysis of the Transformants," China Biotechnology, 28(3):38-43 (2008).
Van Nieuwerburgh et al., "Quantitation of artemisinin and its biosynthetic precursors in *Artemisia annua* L. By high performance liquid chromatography-electrospray quadrupole time-of-flight tandem mass spectrometry," Journal of Chromatography A, 1118:180-187 (2006).
Wu et al., "Redirection of cytosolic or plastidic isoprenoid precursors elevates terpene production in plants," Nature Biotechnology, 24(11):1441-1447 (2006).

* cited by examiner

*Primary Examiner* — Ashwin Mehta
*Assistant Examiner* — Jason Deveau Rosen
(74) *Attorney, Agent, or Firm* — Winston & Strawn LLP

(57) ABSTRACT

The invention relates to a method of utilizing the pts gene and antisense ads to increase patchouli alcohol content in *Artemisia annua* L. plants. Using transgenic *Artemisia annua* L. plants, the method of the invention consistently increases the patchouli alcohol content in those plants, thus laying down a solid foundation for large-scale production of patchouli alcohol and other secondary metabolites such as terpenes other than artemisinin.

5 Claims, No Drawings

METHOD OF UTILIZING THE PTS GENE AND ANTI-SENSE ADS TO INCREASE PATCHOULI ALCOHOL CONTENT IN *ARTEMISIA ANNUA* L

This application claims the benefit of U.S. provisional applications Nos. 61/354,585 filed Jun. 14, 2010 and 61/352,549 filed Jun. 8, 2010.

FIELD OF THE INVENTION

The invention relates to a method of increasing patchouli alcohol content in *Artemisia annua* L. using biotechnology. Specifically, the method of the invention utilizes the patchoulol synthase (pts) gene and antisense Amorpha-4,11-diene synthase (ads) gene to increase the patchouli alcohol content in *Artemisia annua* L. plants.

BACKGROUND OF THE INVENTION

*Artemisia annua* L., also know as Sweet Wormwood, is an annual herb that belongs to the wormwood family *Artemisia*. Artemisinin, a sequiterpene lactone compound that contains a peroxide bridge structure, is isolated form the above-ground portion of the *Artemisia annua* L. plant. Presently, artemisinin is recognized worldwide as the most effective pharmaceutical drug for malaria, especially for cerebral malaria and chloroquine-resistant malaria. Amorpha-4,11-diene synthase (Ads) is a key enzyme in the synthesis pathway of artemisinin, as well as an important target for bio-engineering of artemisinin metabolism. Using genetic engineering tools, in particular, antisense RNA to suppress the expression of the ads gene, will lead to *Artemisia annua* L. plants that do not produce artemisinin or produce less artemisinin. Due to the redistribution of the metabolism stream to the synthesis of secondary metabolites such as other terpenes, those *Artemisia annua* L. plants will have increased production of those secondary metabolites.

Patchoulol (patchouli alcohol) is commonly known in China as Bye Cho Lee alcohol. It has a molecular weight of 222 and its melting point is between 55° C.-59° C. The molecular formula of patchouli alcohol is $C_{15}H_{26}O$. It dissolves easily in organic solvents such as ethanol, acetone, petroleum ether, but not in water. Patchouli alcohol is a natural monomer with a special fragrant smell. It is extracted from *Pogostemon cablin* and used for fragrance and perfume. As defined by French Standard Committee, patchouli alcohol is a significant component in fragrance. It can also be used to treat fungal skin diseases or serve as starting materials for the synthesis of other synthetic compounds. Thus, increasing patchouli alcohol production has a significant commercial value as well as broad market prospects. As a key enzyme in the synthesis pathway of patchouli alcohol in *Pogostemon cablin*, Pts is an important target for bio-engineering of patchouli alcohol metabolism. Applying genetic engineering tools to generate *Artemisia annua* L. plants transformed with the key enzyme pts gene can overcome the "bottleneck" speed limit during patchouli alcohol biosynthesis. Such high-yield *Artemisia annua* L. plants provide a new approach for large-scale production of patchouli alcohol.

In an article entitled "Redirection of Cytosolic or Plastidic Isoprenoid Precursors Elevates Terpene Production in Plants" (Nature Biotechnology, vol. 24, p 1441-1447, 2006), Joe Chappell and colleagues report that, through over-expression of patchoulol synthase, transgenic tobacco plants can produce patchouli alcohol, which is not normally produced by tobacco plants. Moreover, the patchouli alcohol content reaches 0.5 microgram in every gram of wet-weight material. Therefore, it is possible to produce patchouli alcohol in plants that normally do not produce this compound, through metabolic regulation of the key steps of the patchouli alcohol synthesis pathway.

However, there are no currently available technologies in the literature that relate to increasing the patchouli alcohol content by utilizing the pts gene and antisense ads.

SUMMARY OF THE INVENTION

The invention provides a method of utilizing the pts gene and antisense ads to increase patchouli alcohol content in *Artemisia annua* L. plants. According to the method of the invention, three sequences, i.e., the complete open reading frame of the ads gene, the complete open reading frame of the pts gene, and the tp fragment of the plastid targeted signal peptide in *Arabidopsis*, are first obtained. Then, plant expression vectors that contain antisense ads and the plastid targeted pts gene are constructed by linking said ads gene backwards and the plastid targeted pts gene forwards, respectively, to transcription regulatory sequences, which are used simultaneously to transform *Agrobacterium tumefaciens*. The vector-transformed *Agrobacterium tumefaciens* are then used to transform *Artemisia annua* L. plants. The transformed plants are then analyzed with PCR assays to obtain transgenic *Artemisia annua* L. plants. Finally, the patchouli alcohol content in the transgenic *Artemisia annua* L. plants is determined, preferably by high performance liquid chromatography with evaporative light scattering detection (HPLC-ELSD) using a C-18 reverse phase silica gel chromatography column, wherein the mobile phase is a mixture of methyl alcohol and water; the column temperature is 30° C.; the flow rate is 1.0 mL/min; the sample size is 10 μl; the drift-tube temperature of the evaporative light scattering detector is 40° C.; the amplification coefficient is 7; the pressure of the carrier gas is 5 bar; and the volume ratio of methyl alcohol and water in the mobile phase is 70:30.

In one preferred embodiment, the plastid targeted pts gene is under the control of the promoter of the p35S gene or the cyp71ac1 gene.

Preferably, the PCR analysis comprises designing and synthesizing primers for detecting antisense ads and the plastid targeted pts gene, respectively; amplifying DNA and observing the positive DNA band under the Ultraviolet ray so as to determine the transgenic plants.

DETAILED DESCRIPTION OF THE PREFERRED EMBODIMENTS

The objective of the invention is to remedy the deficiencies of the art, by providing a method of utilizing the pts gene and antisense ads to increase the patchouli alcohol content in *Artemisia annua* L. plants. Using transgenic *Artemisia annua* L. plants, the method of the invention consistently increases the patchouli alcohol content in those plants, thus laying down a solid foundation for large-scale production of patchouli alcohol and other secondary metabolites such as terpenes other than artemisinin.

In one preferred embodiment, the method of the invention comprises the following steps:

a) obtaining the complete open reading frame sequence of artemisinin biosynthesis pathway key enzyme ads gene, the complete open reading frame sequence of the patchouli alcohol biosynthesis pathway key enzyme pts gene, and the tp fragment of the plastid targeted signal peptide of *Arabidopsis*;

b) constructing plant expression vectors that contain antisense ads and the plastid targeted pts gene by linking the ads gene obtained in Step a) backwards and the plastid targeted pts gene forwards, respectively, to transcription regulatory sequences;

c) transforming *Agrobacterium tumefaciens* simultaneously with expression vectors containing antisense ads and the plastid targeted pts gene to obtain *Agrobacterium tumefaciens* for transforming *Artemisia annua* L. plants;

d) transforming *Artemisia annua* L. plants with the vector-transformed *Agrobacterium tumefaciens* obtained in Step c) and analyzing the transformed plants with PCR to obtain transgenic *Artemisia annua* L. plants; and e) determining the patchouli alcohol content in the transgenic *Artemisia annua* L. plants.

In a preferred embodiment, the plastid targeted pts gene is under the control of the promoter of the p35S gene or the cyp71ac1 gene. The PCR analysis preferably comprises designing and synthesizing primers for detecting antisense ads and the plastid targeted pts gene, respectively; amplifying DNA and observing the positive DNA band under the Ultraviolet ray so as to determine the transgenic plants.

Preferably, the patchouli alcohol content in the transgenic *Artemisia annua* L. plants is determined by high performance liquid chromatography with evaporative light scattering detection (HPLC-ELSD). More preferably, the chromatography column is a C-18 reverse phase silica gel column; the mobile phase is a mixture of methyl alcohol and water; the column temperature is 30° C.; the flow rate is 1.0 mL/min; the sample size is 10 μl; the drift-tube temperature of the evaporative light scattering detector is 40° C.; the amplification coefficient is 7; and the pressure of the carrier gas is 5 bar. Most preferably, the volume ratio of methyl alcohol and water in the mobile phase is 70:30.

In the method of the invention, the complete open reading frame sequence of the patchoulol synthase pts gene is cloned from *Pogostemon cablin*. Then, a plant expression vector containing the plastid targeted pts gene is constructed and introduced into *Artemisia annua* L. plants mediated by *Agrobacterium tumefaciens*. The complete open reading frame sequence of the Amorpha-4,11-diene synthase ads gene is cloned from *Artemisia annua* L. plants and linked backwards to a transcription regulatory sequence. The plastid targeted pts gene and antisense ads are then simultaneously introduced into the plants and carried to the next generation. The PCR assay is used to determine the plastid targeting of the foreign target gene pts and antisense ads, and the HPLC-ELSD analysis is employed to determine the patchouli alcohol content of the transgenic plants.

The present invention has multiple beneficial effects. By introducing antisense ads and the plastid targeted patchouli alcohol biosynthesis pathway key enzyme pts gene into *Artemisia annua* L. plants, transgenic *Artemisia annua* L. plants can be obtained, which have significantly increased patchouli alcohol content. In particular, the patchouli alcohol content of the transgenic *Artemisia annua* L. plants can reach 0.85% of the wet weight, 850 times as much as that of the non-transgenic wildtype *Artemisia annua* L. plants. Therefore, the invention is significant for the large-scale production of patchouli alcohol as well as the production of secondary metabolites such as terpenes other than artemisinin using transgenic *Artemisia annua* L. plants.

The *Agrobacterium tumefaciens* EHA105 used in the invention has been published in a research article on *Agrobacterium tumefaciens* mediated genetic transformation of fungi (Ya-li Wang et al., Chinese Bio-engineering Journal, 28(3): 38-43, 2008). The *Agrobacterium tumefaciens* EHA105 is also available commercially. For example, it can be obtained from CAMBIA, an Australian company, with the bacterial strain serial no. Gambar1.

EXAMPLES

The invention is described in some detail below for purposes of clarity and understanding. The following examples are intended to illustrate the preferred embodiments of the invention without limiting the scope as a result. It will be appreciated by one skilled in the art, from a reading of the disclosure, that various changes in form and detail can be made without departing from the true scope of the invention in the appended claims. For the experimental conditions that are not specified, it should be understood that standard conditions, such as conditions specified in "Molecular Cloning: A Laboratory Manual" (Sambrook et al., Cold Spring Harbor Laboratory Press, $2^{nd}$ Edition, 1989), or conditions suggested by the manufacturers are used.

Example 1

Step a): Molecular Cloning of Antisense ads of *Artemisia annua* L., the pts Gene and the tp Gene (i) Isolation of Total RNA from *Artemisia annua* L.

A small quantity of young tender leaves were collected from *Artemisia annua* L. plants, immediately frozen in liquid nitrogen and grounded using a mortar and pestle. The grounded leaves were then transferred to a 1.5 ml Eppendorf tube which contains 1 ml TRIzol Reagents (Gibco BRL, USA). After vortexing thoroughly, the sample was incubated for 5 min at room temperature. After adding 200 ul of chloroform to the sample, cap the sample tube was capped securely and vortexed vigorously for 15 sec. The sample was then incubated at room temperature for 2-3 min and centrifuged at 12,000 g for 15 min at 4° C. Following centrifugation, the upper aqueous phase (~600 ul) was transferred into a fresh 1.5 ml Eppendorf tube and equal volume isopropanol was added. The tube was turned upside-down to mix the sample thoroughly and then the sample was incubated at room temperature for 10 min and centrifuged at 12,000 g for 10 min at 4° C. The supernatant was removed completely and the RNA pellet was washed with 1 ml of 75% (v/v) ethanol. The sample was then vortexed and centrifuged at 7,500 g for 5 min at 4° C. The RNA pellet was air-died at room temperature for 15-20 min and then dissolved in 30-50 ul RNase-free water. The quality of the total RNA was evaluated by denaturing formaldehyde gel electrophoresis and the quantity of the total RNA was determined by spectrophotometric analysis.

(ii) Isolation of Total RNA from *Pogostemon cablin*

A small quantity of young tender leaves were collected from *Pogostemon cablin* plants, immediately frozen in liquid nitrogen and grounded using a mortar and pestle. The grounded leaves were then transferred to a 1.5 ml Eppendorf tube which contains 1 ml TRIzol Reagents (Gibco BRL, USA). After vortexing thoroughly, the sample was incubated for 5 min at room temperature. After adding 200 ul of chloroform to the sample, cap the sample tube was capped securely and vortexed vigorously for 15 sec. The sample was then incubated at room temperature for 2-3 min and centrifuged at 12,000 g for 15 min at 4° C. Following centrifugation, the upper aqueous phase (~600 ul) was transferred into a fresh 1.5 ml Eppendorf tube and equal volume isopropanol was added. The tube was turned upside-down to mix the sample thoroughly and then the sample was incubated at room temperature for 10 min and centrifuged at 12,000 g for 10 min at 4° C. The supernatant was removed completely and the RNA pellet was washed with 1 ml of 75% (v/v) ethanol. The sample was then vortexed and centrifuged at 7,500 g for 5 min at 4° C. The RNA pellet was air-died at room temperature for 15-20 min and then dissolved in 30-50 ul RNase-free water. The quality of the total RNA was evaluated by denaturing formaldehyde gel electrophoresis and the quantity of the total RNA was determined by spectrophotometric analysis.

(iii) Isolation of Total RNA from *Arabidopsis*

A small quantity of young tender leaves were collected from *Arabidopsis* plants, immediately frozen in liquid nitrogen and grounded using a mortar and pestle. The grounded leaves were then transferred to a 1.5 ml Eppendorf tube which contains 1 ml TRIzol Reagents (Gibco BRL, USA). After vortexing thoroughly, the sample was incubated for 5 min at room temperature. After adding 200 ul of chloroform to the sample, cap the sample tube was capped securely and vortexed vigorously for 15 sec. The sample was then incubated at room temperature for 2-3 min and centrifuged at 12,000 g for 15 min at 4° C. Following centrifugation, the upper aqueous phase (~600 ul) was transferred into a fresh 1.5 ml Eppendorf tube and equal volume isopropanol was added. The tube was turned upside-down to mix the sample thoroughly and then the sample was incubated at room temperature for 10 min and centrifuged at 12,000 g for 10 min at 4° C. The supernatant was removed completely and the RNA pellet was washed with 1 ml of 75% (v/v) ethanol. The sample was then vortexed and centrifuged at 7,500 g for 5 min at 4° C. The RNA pellet was air-died at room temperature for 15-20 min and then dissolved in 30-50 ul RNase-free water. The quality of the total RNA was evaluated by denaturing formaldehyde gel electrophoresis and the quantity of the total RNA was determined by spectrophotometric analysis.

(iv) Cloning of the ads Gene of *Artemisia annua* L.

The isolated total RNA from *Artemisia annua* L. was reverse transcribed using reverse transcriptase XL (AMV) to obtain the first strand cDNA. Based on the *Artemisia annua* L. ads gene coding sequence (SEQ ID NO.: 1), design upstream and downstream primers to amplify the complete open reading frame, and introduce restriction enzyme sites SacI and BamHI, respectively, on the upstream and downstream primers, for constructing expression vectors. After PCR amplification using the first strand cDNA as the template, check the sequence of the PCR products. The DNA sequencing was conducted by Shanghai Yin Jun Biotechnology Ltd, Inc., using a 3730 DNA Sequencer. The sequencing result indicates that the cloned partial sequence is the same as the coding sequence of the *Artemisia annua* L. ads gene (SEQ ID NO.: 1) reported in GenBank.

(v) Cloning of the pts Gene of *Pogostemon cablin*

The isolated total RNA from *Pogostemon cablin* was reverse transcribed using reverse transcriptase XL (AMV) to obtain the first strand cDNA. Based on the *Pogostemon cablin* pts gene coding sequence (SEQ ID NO.: 2), design upstream and downstream primers to amplify the complete open reading frame, and introduce restriction enzyme sites NcoI and SacI, respectively, on the upstream and downstream primers, for constructing expression vectors. After PCR amplification using the first strand cDNA as the template, check the sequence of the PCR products. The DNA sequencing was conducted by Shanghai Yin Jun Biotechnology Ltd, Inc., using a 3730 DNA Sequencer. The sequencing result indicates that the cloned sequence is the same as the coding sequence of the *Pogostemon cablin* pts gene (SEQ ID NO.: 2) reported in GenBank.

(vi) Cloning of the tp Gene of *Arabidopsis*

The isolated total RNA from *Arabidopsis* was reverse transcribed using reverse transcriptase XL (AMV) to obtain the first strand cDNA. Based on the *Arabidopsis* tp gene coding sequence (SEQ ID NO.: 3), design upstream and downstream primers to amplify a sequence retaining the complete function, and introduce restriction enzyme sites SacI and BamHI, respectively, on the upstream and downstream primers, for constructing expression vectors. After PCR amplification using the first strand cDNA as the template, check the sequence of the PCR product. The DNA sequencing was conducted by Shanghai Yin Jun Biotechnology Ltd, Inc., using a 3730 DNA Sequencer. The sequencing result indicates that the cloned sequence is the same as the coding sequence of the *Arabidopsis* tp gene (SEQ ID NO.: 3) reported in GenBank.

Step b): Construction of Plant Bipartite Expression Vectors Containing the Plastid Targeted pts Gene and Antisense ads (i) Construction of Intermediate Vector pCAMBIA2300::p35S-gus-nos Use pBI121 and pCAMBIA2300 as the basic elements to construct pCAMBIA2300::p35S-gus-nos bipartite plant expression vector. Digest both the pBI121 and pCAMBIA2300 plasmids with two restriction enzymes, HindIII and EcoRI; retrieve the GUS expression cassette of the pBI121 plasmid and the big fragment of the pCAMBIA2300 plasmid; ligate the retrieved fragments and screen the correct construct by transformation and extracting plasmids to verify through enzyme digestion.

(ii) Construction of Plant Expression Vector pCAMBIA2300::p35S-antisense ads-nos Use pCAMBIA2300::p35S-gus-nos as the expression vector by replacing the gus gene with the reversed ads gene; digest both the pGEM T-easy+antisense ads and the pCAMBIA2300::p35S-gus-nos plasmids with two restriction enzymes, BamHI and SacI; retrieve the antisense ads fragment and the big fragment of the pCAMBIA2300::p35S-gus-nos plasmid; ligate the retrieved fragments and transform; pick single colonies and extract plasmids to verify through PCR analysis and enzyme digestion.

(iii) Construction of Plant Expression Vector pCAMBIA2300::p35S-tp-pts-nos

Use pCAMBIA2300::p35S-gus-nos as the expression vector by replacing the gus gene with the tp-pts gene; digest both the pGEM T-easy+tp-pts and the pCAMBIA2300::p35S-gus-nos plasmids, retrieve the tp-pts fragment and the big fragment of the pCAMBIA2300::p35S-gus-nos plasmid; ligate the retrieved fragments and transform; pick single colonies and extract plasmids to verify through PCR analysis and enzyme digestion.

Step c): Transformation of *Agrobacterium tumefaciens* with Plant Expression Vectors Containing Antisense Ads and the Plastid Targeted pts Gene Transform *Agrobacterium tumefaciens*, such as EHA105, with bipartite plant expression vectors containing antisense ads and the plastid targeted pts gene obtained in Step b). Add 1 ug of plasmid DNA to 200 ml EHA105 competent cells, mix well and incubate on ice for 30 min followed by incubating at −70° C. for 10 min; incubate in 37° C. bath for 5 min or 42° C. bath for 1 min followed by incubating on ice for 2 min; add the cells to a flask containing 800 ml Luria Broth (LB) liquid medium and culture in an orbital shaker at 28° C. and 175 rpm for 3 hr; plate out the culture on LB plates containing 50 ug/ml Kanamycin; and incubate at 28° C. until single colonies appear.

Step d): *Agrobacterium tumefaciens* Mediated Transformation of *Artemisia annua* L. Plants (i) Pre-cultivation of the Explants Soak *Artemisia annua* L. seeds in 75% (v/v) ethanol for 1 min followed by soaking in 20% (v/v) NaCl for 20 min; wash with sterile water for 3-4 times; blot the surface water with aseptic blotting paper; inoculate on hormone-free MS solid medium, which was discovered by Murashige and Skoog in 1962 and commercially available; cultivate at 25° C. with 16 hr light and 8 hr darkness for 3 days to obtain aseptic *Artemisia annua* L. seedling; cut leaves from aseptic seedlings when they reach 5 cm to use as explants for transformation.

(ii) Co-cultivation of *Agrobacterium tumefaciens* and *Artemisia annua* L.

Transfer said leave explants to the cultivation medium comprising ½ MS and 100 umol/L AS for co-cultivation; add drop-wise activated ½ MS suspension of *Agrobacterium tumefaciens* transformed with plant bipartite expression vectors containing antisense ads and the plastid targeted pts gene; make sure that there is sufficient contact between the explants and the suspension; cultivate in dark at 28° C. for 3 days, using the leave explants contacting *Agrobacterium tumefaciens* without the target genes as control.

(iii) Screen Kanamycin-Resistant Shoots

Transfer said *Artemisia annua* L. explants which have been co-cultivated for 3 days to shoot selection medium, consisting of MS, 0.5 mg/L 6-BA, 0.05 mg/L NAA, 50 mg/L kanamycin and 500 mg/L Cb, at 25° C. and 16 h/8 h light cycle; subculture the cultures to fresh selection medium every two weeks to obtain kanamycin-resistant shoots after 2-3 generations; isolate the meritstems from the healthy kanamycin-resistant regenerated shoots and cultivate in ½ MSO and 125 mg/L Cb rooting medium to grow roots, so as to obtain kanamycin-resistant *Artemisia annua* L. plants.

(iv) PCR Analysis of Transgenic *Artemisia annua* L. Plants

Forward primer and reverse primers for detecting the target gene were designed based on the p35S and antisense ads sequences of the p35s-antisense ads-nos expression cassette. Using the specifically designed primers, it is possible to amplify a 1882 bp unique fragment from DNA templates of the transgenic plants, but not from those of non-transgenic *Artemisia annua* L. genome.

Forward primer and reverse primers for the target gene were designed based on the p35S and tp-pts sequences of the p35s-tp-pts-nos expression cassette. Using the specifically designed primers, it is possible to amplify a 2966 bp unique fragment from DNA templates of the transgenic plants, but not from those of non-transgenic *Artemisia annua* L. genome.

Step e): Determining the Patchouli Alcohol Content in Transgenic *Artemisia annua* L. Plants Using HPLC-ELSD Analysis (i) HPLC-ELSD Conditions and the Suitability of this System for the Intended Assays as well as Preparation of Standard Liquids HPLC: The Water Alliance 2695 System and the C-18 reverse phase silica gel chromatography column, which is produced by Waters (SymmetrySheild™ C18), were used. The specifications are as follows:

membrane thickness: 5 um;

length×inner radius: 250 mm×4.6 mm;

mobile phase: a mixture of methyl alcohol and water having the volume ratio of 70:30 such that the retention time of patchouli alcohol is 5.1 min with a fine peak;

column temperature: 30° C.;

flow rate: 1.0 mL/min;

sample size: 10 µl;

sensitivity AUFS: 1.0.

Theoretical plate count based on patchouli alcohol peak is no less than 2000.

ELSD: The Water Alliance 2420 system was used. The drift-tube temperature of the evaporative light scattering detector was 40° C., the amplification coefficient was 7, and the pressure of the carrier gas was 5 bar.

2.0 mg patchouli alcohol standard from Sigma was taken and dissolved in 1 ml methyl alcohol to produce a 2 mg/ml patchouli alcohol standard solution, which was stored at −20° C. to be used later.

(ii) Preparation of Standard Curve

Load 2 ul, 4 ul, 6 ul, 8 ul and 10 ul control sample solutions, respectively, at corresponding chromatography conditions; record the graphic parameters and the column parameters; carry out return analysis based on peak area (Y) and standard content (X, ug). The result indicates that patchouli alcohol shows good log-log linear correlation at the range of 4 ug-20 ug. The log-log linear return formula for patchouli alcohol is Y=1.28e+000X+4.71e+000, R=0.979546.

(iii) Preparation of Samples and Determining Patchouli Alcohol Content

The process of extracting patchouli alcohol is based on a report by Van Nieuwerburgh et al. (Journal of Chromatography A, 1118 (2):180-187, Jun. 23, 2006). Soak 1-2 g fresh *Artemisia annua* L. leaves in 10 ml chloroform in a 50 ml test tube and shake for 1 min; transfer the solution to a fresh tube to let the chloroform evaporate; add 3 ml water-free alcohol to dissolve the extract for HPLC analysis; use high performance liquid phase chromatography and evaporative light scattering detector to determine the patchouli alcohol content, with the sample loading size being 20 ul; substitute the peak area in the linear return formula to calculate the patchouli alcohol content in the sample (mg); and divide the result by the wet weight of the *Artemisia annua* L. leaves (g) to arrive at the patchouli alcohol content of the *Artemisia annua* L. plant.

The result indicates that in this experiment, the patchouli alcohol content of the transgenic *Artemisia annua* L. plant is 0.8% of the wet weight, which is 800 times as much as that of the non-transgenic wildtype *Artemisia annua* L. plants.

Example 2

In this experiment, Steps a), c) and e) are the same as those of Example 1. The differences of these two experiments are shown below:

Step b) is the Same as That of Example 1 Except That:

(iii) Construction of Intermediate Vector pCAMBIA2300::cyp71av1-gus-nos

Use pCAMBIA2300::p35S-gus-nos as the expression vector by replacing the p35s promoter with the cyp71av1 promoter; digest both the pGEM T-easy+cyp71av1 promoter and the pCAMBIA2300::p35S-gus-nos plasmids with two restriction enzymes, PstI and BamHI; retrieve the cyp71av1 promoter fragment and the big fragment of the pCAMBIA2300::p35S-gus-nos plasmid; ligate the retrieved fragments and transform; pick single colonies and extract plasmids to verify through PCR analysis and enzyme digestion.

(iv) Construction of Plant Expression Vector pCAMBIA2300:: cyp71av1 Promoter-tp-pts-nos Use pCAMBIA2300:: cyp71av1 promoter-gus-nos as the expression vector by replacing the gus gene with the tp-pts gene; digest both the pGEM T-easy+tp-pts and the pCAMBIA2300::cyp71av1 promoter-gus-nos plasmids with two restriction enzymes, BamHI and SacI; retrieve the tp-pts fragment and the big fragment of the pCAMBIA2300:: cyp71av1 promoter-gus-nos plasmid; ligate the retrieved fragments and transform; pick single colonies and extract plasmids to verify through PCR analysis and enzyme digestion.

Step d) is the Same as That of Example 1 Except That:

(iv) PCR Analysis of Transgenic *Artemisia annua* L. Plants

Forward primer and reverse primers for detecting the target gene were designed based on the cyp71av1 promoter and antisense ads sequences of the cyp71av1 promoter-antisense ads-nos expression cassette. Using the specifically designed primers, a 1914 bp unique fragment was amplified from DNA templates of transgenic plants, but not from those of non-transgenic *Artemisia annua* L. genome.

Forward primer and reverse primers for the target gene were designed based on the cyp71av1 promoter and tp-pts sequences of the cyp71av1 promoter-tp-pts-nos expression cassette. Using the specifically designed primers, a 2998 bp unique fragment was amplified from DNA templates of transgenic plants, but not from those of non-transgenic *Artemisia annua* L. genome.

The result indicates that in this experiment, the patchouli alcohol content of the transgenic *Artemisia annua* L. plant is 0.85% of the wet-weight, which is 850 times as much as that of the non-transgenic wildtype *Artemisia annua* L. plants.

What is claimed is:

1. A method of utilizing the pts gene and antisense ads gene to increase patchouli alcohol content in *Artemisia annua* L., said method comprising
   a) obtaining the complete open reading frame sequence of artemisinin biosynthesis pathway key enzyme ads gene of SEQ ID NO: 1, and the complete open reading frame sequence of the patchouli alcohol biosynthesis pathway key enzyme pts gene, set forth in SEQ ID NO: 2, linked to the plastid targeted signal peptide of the *Arabidopsis* tp gene as set forth in SEQ ID NO: 3;
   b) constructing plant expression vectors that contain the ads open reading frame in antisense orientation linked to transcriptional regulatory sequences, and the plastid targeted pts gene linked to transcriptional regulatory sequences;
   c) transforming *Agrobacterium tumefaciens* simultaneously with expression vectors containing the antisense ads and the plastid targeted pts gene to obtain *Agrobacterium tumefaciens* for transforming *Artemisia annua* L. plants;
   d) transforming *Artemisia annua* L. plants with the vector-transformed *Agrobacterium tumefaciens* obtained in Step c) and analyzing the transformed plants with PCR to obtain transgenic *Artemisia annua* L. plants; and
   e) determining the patchouli alcohol content in the transgenic *Artemisia annua* L. plants.

2. The method of claim 1, wherein the plastid targeted pts gene is under the control of the promoter of the p35S gene or the cyp71ac1 gene.

3. The method of claim 1, wherein the PCR analysis in Step d) comprises designing and synthesizing primers for detecting antisense ads and the plastid targeted pts gene, respectively; amplifying DNA and observing the positive DNA band under the Ultraviolet ray so as to screen the transgenic plants.

4. The method of claim 1, wherein Step e) is performed by high performance liquid chromatography with evaporative light scattering detection (HPLC-ELSD), wherein the chromatography column is C-18 reverse phase silica gel column; the mobile phase is a mixture of methyl alcohol and water; the column temperature is 30° C.; the flow rate is 1.0 mL/min; the sample size is 10 μl; the drift-tube temperature of the evaporative light scattering detector is 40° C.; the amplification coefficient is 7; and the pressure of the carrier gas is 5 bar.

5. The method of claim 4, wherein the volume ratio of methyl alcohol and water in the mobile phase is 70:30.

* * * * *

SEQUENCE LISTING

<160> NUMBER OF SEQ ID NOS: 3

<210> SEQ ID NO 1
<211> LENGTH: 1641
<212> TYPE: DNA
<213> ORGANISM: Artemisia annua L.

<400> SEQUENCE: 1

```
atgtcactta cagaagaaaa acctattcgc cccattgcca actttcctcc aagcatttgg      60
ggagatcagt ttctcatcta tgaaaagcaa gtagagcaag gggtggaaca gatagtgaat     120
gatttaaaaa aagaagtgcg gcaactacta aaagaagctt tggatattcc tatgaaacat     180
gccaatttat tgaagctgat tgatgaaatc caacgccttg gaataccgta tcactttgaa     240
cgggagattg atcatgcatt gcaatgtatt tatgaaacat atggtgataa ctggaatggt     300
gaccgctctt ccttatggtt ccgtcttatg cgaaagcaag gatattatgt tacatgtgat     360
gttttcaata actataaaga caaaaatgga gcgttcaagc aatcgttagc taatgatgtt     420
gaaggtttgc ttgagttgta cgaagcaact tctatgaggg tacctgggga gattatatta     480
gaagatgctc ttggttttac acgatctcgt cttagcatta tgacaaaaga tgcttttttct     540
acaaaccccg ctcttttttac cgaaatacaa cgggcactaa agcaacccct ttggaaaagg     600
ttgccaagaa tagaggcggc gcagtacatt cctttctatc aacaacaaga ttctcataac     660
aagactttac ttaaacttgc taagttagag ttcaatttgc ttcagtcatt gcacaaggaa     720
gagctcagcc atgtgtgcaa atggtggaaa gctttcgata tcaagaagaa cgcaccttgt     780
ttaagagata gaattgttga atgctacttt tggggactag gttcaggcta tgagccacag     840
tattcccggg ctagagtttt cttcacaaaa gctgttgctg ttataactct tatagatgac     900
acttatgatg cgtatggtac ttatgaagaa cttaagatct ttactgaagc tgttgaaagg     960
tggtcaatta catgcttaga cacacttcca gaatacatga aaccgatata caaattattc    1020
atggatacat acacagaaat ggaagaattt cttgcaaagg agggaagaac agatctattt    1080
aactgcggca aagaatttgt gaaagagttt gttagaaacc tgatggttga agcaaaatgg    1140
gcaaatgagg gacacatacc aaccactgaa gagcatgatc cagttgtaat cattactggc    1200
ggtgctaacc tgcttacaac aacttgttat cttggcatga gtgatatatt cacaaaagag    1260
tctgtcgaat gggctgtctc tgcacctcct cttttagat actcaggtat acttggtcga    1320
cgcctaaatg atctcatgac ccacaaggcc gagcaagaaa gaaaacatag ttcatcgagc    1380
cttgaaagtt atatgaagga atataatgtc aatgaggagt atgcccaaac cttgatttac    1440
aaggaagtag aagatgtgtg gaaagatata aaccgagagt acctcacaac taaaaacatt    1500
ccaaggccgt tattgatggc tgtgatctat ttgtgccagt tccttgaagt tcaatatgca    1560
ggaaaggata acttcacacg tatgggagac gaatacaaac atctcataaa gtctctactc    1620
```
gtttatccta tgagtatatg a                                              1641

<210> SEQ ID NO 2
<211> LENGTH: 1689
<212> TYPE: DNA
<213> ORGANISM: Pogostemon cablin

<400> SEQUENCE: 2
gggggaagat ctagctgcat gaaggagctc atggagttgt atgcccaaag tgttggagtg     60
ggtgctgctt ctcgtcctct tgcgaatttt catccatgtg tgtggggaga caaattcatt    120
gtctacaacc cacaatcatg ccaggctgga gagagagaag aggctgagga gctgaaagtg    180
gagctgaaaa gagagctgaa ggaagcatca gacaactaca tgcggcaact gaaaatggtg    240
gatgcaatac aacgattagg cattgactat cttttgtgg aagatgttga tgaagctttg     300
aagaatctgt ttgaaatgtt tgatgctttc tgcaagaata tcatgacat gcacgccact      360 gctctcagct ttcgccttct cagacaacat ggatacagag tttcatgtga agttttgaa     420 aagtttaagg atggcaaaga tggatttaag gttccaaatg aggatggagc ggttgcagtc    480
cttgaattct tcgaagccac gcatctcaga gtccatggaa aagacgtcct tgataatgct    540
tttgacttca ctaggaacta cttggaatca gtctatgcaa ctttgaacga tccaaccgcg    600
aaacaagtcc acaacgcatt gaatgagttc tcttttcgaa gaggattgcc acgcgtggaa    660
gcaaggaagt acatatcaat ctacgagcaa tacgcatctc atcacaaagg cttgctcaaa    720
cttgctaagc tggatttcaa cttggtacaa gcttttgcaca aagggagct gagtgaagat     780 tctaggtggt ggaagacttt acaagtgccc acaaagctat cattcgttag agatcgattg    840
gtggagtcct acttctgggc ttcgggatct tatttcgaac cgaattattc ggtagctagg    900
atgattttag caaaagggct ggctgtatta tctcttatgg atgatgtgta tgatgcatat    960
ggtacttttg aggaattaca aatgttcaca gatgcaatcg aaaggtggga tgcttcatgt   1020
ttagataaac ttccagatta catgaaaata gtatacaagg ccttttgga tgtgtttgag    1080 gaagttgacg aggagttgat caagctaggc gcaccatatc gagcctacta tggaaaagaa   1140
gccatgaaat acgccgcgag agcttacatg gaagaggccc aatggaggga gcaaaagcac   1200
aaacccacaa ccaaggagta tatgaagctg gcaaccaaga catgtggcta cataactcta   1260
ataatattat catgtcttgg agtggaagag ggcattgtga ccaaagaagc cttcgattgg   1320
gtgttctccc gacctccttt catcgaggct acattaatca ttgccaggct cgtcaatgat   1380
attacaggac acgagtttga gaaaaaacga gagcacgttc gcactgcagt agaatgctac   1440
atggaagagc acaaagtggg gaagcaagag gtggtgtctg aattctacaa ccaaatggag   1500
tcagcatgga aggacattaa tgaggggttc ctcagaccag ttgaatttcc aatccctcta   1560
ctttatctta ttctcaattc agtccgaaca cttgaggtta tttacaaaga gggcgattcg   1620
tatacacacg tgggtcctgc aatgcaaaac atcatcaagc agttgtacct tcaccctgtt   1680
ccatattaa                                                           1689

<210> SEQ ID NO 3
<211> LENGTH: 177
<212> TYPE: DNA
<213> ORGANISM: Arabidopsis

<400> SEQUENCE: 3
atggcttcct ctatgctctc ctccgccgct gtggttacat ccccggctca ggccaccatg     60

```
gtcgctccat tcaccggctt gaagtcatcc gctgcattcc cggtcacccg caagaccaac     120
aaggacatca cttccatcgc aagcaacggg ggaagatcta gctgcatgaa ggagctc        177
```